United States Patent [19]

Hornor

[11] Patent Number: 5,552,350
[45] Date of Patent: Sep. 3, 1996

[54] LOW-FUSING TEMPERATURE PORCELAIN

[75] Inventor: John A. Hornor, Sicklerville, N.J.

[73] Assignee: Ceramco Inc., Burlington, N.J.

[21] Appl. No.: 354,385

[22] Filed: Dec. 12, 1994

[51] Int. Cl.⁶ .............................. C03C 8/02; C03C 3/095
[52] U.S. Cl. .................. 501/64; 501/66; 501/70; 501/21; 106/35
[58] Field of Search .................... 501/66, 70, 64, 501/21; 106/35

[56] References Cited

U.S. PATENT DOCUMENTS

| | | | |
|---|---|---|---|
| 4,170,823 | 10/1979 | Smyth et al. | 32/8 |
| 4,481,036 | 11/1984 | Panzera | 501/70 X |
| 4,798,536 | 1/1989 | Katz | 106/35 X |
| 5,346,866 | 9/1994 | Komma et al. | 501/64 X |
| 5,387,558 | 2/1995 | Grossman | 501/64 X |
| 5,432,130 | 7/1995 | Rheinberger et al. | 501/70 X |

*Primary Examiner*—Karl Group
*Attorney, Agent, or Firm*—James B. Bieber

[57] ABSTRACT

A low-fusing temperature porcelain composition for use in dental prostheses is disclosed having a fusing temperature of about 700° C.±50° C. and a coefficient of thermal expansion compatible with a substrate of metal or ceramic. The composition includes, in weight percent of the composition, $SiO_2$ at 57–61, $Al_2O_3$ at 6.5–11.5, $Na_2O$ at 10–11, $K_2O$ at 8–16, $Li_2O$ at 1–3, CaO at 1.5–4, BaO at 1.5–2.5, $CeO_2$ at 0.5–2, and $Tb_2O_3$ at 0.5–2.

4 Claims, No Drawings

LOW-FUSING TEMPERATURE PORCELAIN

FIELD OF THE INVENTION

The invention relates to porcelains used in dental prostheses. More particularly the invention relates to a low-fusing temperature porcelain suitable for use in combination with metal or porcelain substrates.

BACKGROUND OF THE INVENTION

A dental prosthesis often comprises a crown or bridge restoration in which a dental porcelain is fused to a supporting metal or ceramic substrate. Dental porcelains are generally a mixture of glass frit components or natural feldspars or the like. There are a number of key considerations in selecting frit components to form a porcelain that will be compatible with the selected substrate.

For example, the porcelain must have a coefficient of thermal expansion that is as close as possible to that of the substrate. Otherwise, a porcelain fused to the substrate will tend to crack and separate from its supporting structure.

Another key factor in selecting a porcelain component is its effect upon processing temperature of the porcelain; that is, the temperature that must be utilized in fusing the porcelain to the substrate. Fusing temperatures of porcelain materials of the prior art have generally been on the order of 900° C. or higher. Such elevated temperatures limit the composition of the substrate that may be used since some alloys or ceramic compositions will distort or otherwise suffer detrimental compositional changes under such processing conditions.

In selecting glass components and their amounts in the porcelain composition to achieve low-fusing temperatures and appropriate coefficients of thermal expansion, care also must be exercised to insure that the changes in composition do not otherwise adversely effect the qualities of the resulting fired porcelain with respect to its performance in a dental environment. Such characteristics of concern are acid resistance, hardness, flexural strength and the like.

Thus, heretofore, it has remained the goal of researchers to produce a porcelain glass frit composition that has a low-fusing or processing temperature and a coefficient of thermal expansion such that it can be used in combination with both metal and porcelain substrates in dental prostheses. Such a composition would have improved versatility for use in making, repairing or improving crowns, bridges, linings for dentures or as finish porcelains and stains.

SUMMARY OF THE INVENTION

A low-fusing temperature porcelain composition for use in a dental prosthesis is provided. The porcelain composition comprises:

| Frit Components | Weight Percent |
|---|---|
| $SiO_2$ | 57–61 |
| $Al_2O_3$ | 6.5–11.5 |
| $Na_2O$ | 10–12 |
| $K_2O$ | 8–16 |
| $Li_2O$ | 1–3 |
| CaO | 1.5–4 |
| BaO | 1.5–2.5 |
| $CeO_2$ | 0.5–2 |
| $Tb_2O_3$ | 0.5–2 |

The porcelain of the invention has a fusing temperature of about 700° C.± 50° C. and a coefficient of thermal expansion compatible with a substrate of metal or ceramic. Preferably, the coefficient of thermal expansion is about 12–13 $\mu m.K^{-1}$ [20° to 500° C.].

DETAILED DESCRIPTION OF THE INVENTION

The invention is a low-fusing temperature porcelain composition that is a mixture of oxides such that the resulting frit has a fusing temperature of about 700° C.± 50° C. and a coefficient of thermal expansion of 12–13 $\mu m.K^{-1}$ [20° to 500° C.]. The low fusing porcelain may be employed in dental crowns, bridges, restorations and dentures wherein it is fused to a substrate or coping of metal or conventional porcelains, such as Ceramco II®, and dental alloy copings, such as Ceramco II® Silver, both manufactured by Dentsply International Inc. of York, Pa.

The compositional range for the low-fusing temperature dental porcelains of the invention, having processing temperatures of less than about 705° C. and a coefficient of thermal expansion (CTE) of 12–13 $\mu m.K^{-1}$ [20 to 500° C.] is a mixture of oxides having the following composition:

TABLE 1

| Oxide | Weight Percent |
|---|---|
| $SiO_2$ | 57–61 |
| $Al_2O_3$ | 6.5–11.5 |
| $Na_2O$ | 10–12 |
| $K_2O$ | 8–16 |
| $Li_2O$ | 1–3 |
| CaO | 1.5–4 |
| BaO | 1.5–2.5 |
| $CeO_2$ | 0.5–2 |
| $Tb_2O_3$ | 0.5–2 |

An optional ingredient is $B_2O_3$ at about 0–2% by weight of the composition.

The following examples describe preferred compositions and characterize the resulting dental porcelain qualities.

EXAMPLE 1

A single glass frit, low temperature fusing porcelain is made by combining and fusing oxides, and then forming a pulverized mixture, as is well known in the art, of the composition indicated in Table 1. The resulting porcelain has a firing temperature of 705° C. and a CTE of 12.5 $\mu m.K^{-1}$. Samples of the resulting mixture have the characteristics and properties shown in Table 2.

TABLE 2

| Oxide | Weight Percent Ex. 1 |
|---|---|
| $SiO_2$ | 59 |
| $Al_2O_3$ | 7 |
| $Na_2O$ | 10.5 |
| $K_2O$ | 13.5 |
| $Li_2O$ | 2 |
| CaO | 2 |
| BaO | 2 |
| $B_2O_3$ | 2 |
| $CeO_2$ | 1 |
| $Tb_4O_7$ | 1 |
| Total | 100 |
| CTE ($\mu m \cdot K^{-1}$) | 12.5 |

TABLE 2-continued

| Oxide | Weight Percent Ex. 1 |
|---|---|
| (30–500° C.) | |
| Firing Temp. (°C.) | 705 |
| (°F.) | 1300 |

Samples of the low-fusing glass of the invention are also characterized by their low chemical solubility. Chemical solubility was determined by boiling the porcelain samples in acetic acid for sixteen hours. The maximum allowable weight loss per ISO standards is 1.0 µg/mm². The measured weight loss of the glass frit of example 1 of the invention is 0.26 µg/mm². The weight loss of a competitive low-fusing porcelain in the marketplace (Durceram-LFC, manufactured by Degussa of Germany is 0.47 µg/mm².

EXAMPLES 2–4

Low-fusing porcelains of the invention are made in the same manner as Example 1, having the composition indicated in Table 3 below, and the desired characteristics within the scope of the invention.

TABLE 3

| Oxide | Weight Percent | | |
|---|---|---|---|
| | Ex. 2 | Ex. 3 | Ex. 4 |
| $SiO_2$ | 59 | 59 | 57.7 |
| $Al_2O_3$ | 7 | 7 | 11.5 |
| $Na_2O$ | 10 | 10 | 12 |
| $K_2O$ | 16 | 14 | 8 |
| $Li_2O$ | 2 | 2 | 3 |
| CaO | 2 | 2 | 3.8 |
| BaO | 2 | 2 | 2 |
| $B_2O_3$ | — | 2 | — |
| $CeO_2$ | 1 | 1 | 1 |
| $Tb_4O_7$ | 1 | 1 | 1 |
| Total | 100 | 100 | 100 |
| CTE (µm·K$^{-1}$) (30–500° C.) | 12.6 | 12.5 | 12.6 |
| Firing Temp. | | | |
| (°C.) | 705 | 705 | 690 |
| (°F.) | 1300 | 1300 | 1270 |

The examples of the invention when utilized in forming dental prostheses are characterized by having an easier polishability due to the reduced hardness compared to conventional porcelains. The amounts of $CeO_2$ and $Tb_2O_3$ are adjusted to provide desired fluorescence characteristics, ranging from bluish to white fluorescence.

Variations and modifications of the composition are within those skilled in the art, for example, to adjust the coefficient of thermal expansion to match the desired value of 12–13 µm.K$^{-1}$, depending upon the substrate to which the porcelain will be applied.

What is claimed is:

1. A low-fusing temperature porcelain composition for use in a dental prosthesis, consisting essentially of in weight percent of the porcelain composition:

| Oxide | Weight Percent |
|---|---|
| $SiO_2$ | 57–61 |
| $Al_2O_3$ | 6.5–11.5 |
| $Na_2O$ | 10–12 |
| $K_2O$ | 8–16 |
| $Li_2O$ | 1–3 |
| CaO | 1.5–4 |
| BaO | 1.5–2.5 |
| $CeO_2$ | 0.5–2 |
| $Tb_2O_3$ | 0.5–2, | said porcelain having a fusing temperature of about 700° C.±50° C. and a coefficient of thermal expansion compatible with a substrate of metal or ceramic suitable for a dental prothestic.

2. The porcelain of claim 1, having a coefficient of thermal expansion of about 12–13 µm.K$^{-1}$, measured at 20° to 500° C.

3. The porcelain of claim 1, further comprising up to about 2 weight percent by weight of $B_2O_3$.

4. A low-fusing temperature porcelain composition for use in a dental prosthesis, consisting essentially of:

a glass frit, having a processing temperature of about 705° C. and a coefficient of thermal expansion of about 12–13 µm.K$^{-1}$, measured at 20° to 500° C.; and, in weight percent, ± 0.5, of the composition,

| Oxide | Weight Percent |
|---|---|
| $SiO_2$ | 59 |
| $Al_2O_3$ | 7 |
| $Na_2O$ | 10.5 |
| $K_2O$ | 13.5 |
| $Li_2O$ | 2 |
| CaO | 2 |
| BaO | 2 |
| $B_2O_3$ | 2 |
| $CeO_2$ | 1 |
| $Tb_2O_3$ | 1. |

* * * * *